Jan. 23, 1968 R. A. GRIESBACH Plant Pat. 2,791
GLADIOLUS PLANT
Filed Sept. 30, 1966
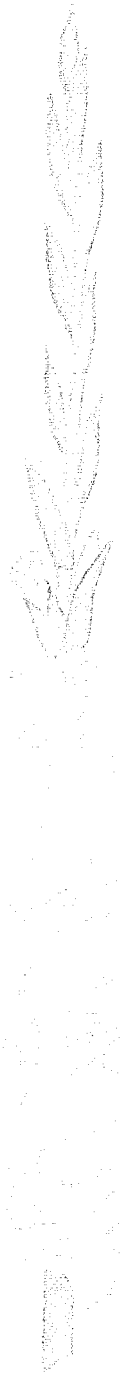
INVENTOR
Robert A. Griesbach
By: Lamont Johnston
ATTORNEY United States Patent Office Plant Pat. 2,791
Patented Jan. 23, 1968

2,791
GLADIOLUS PLANT

Robert A. Griesbach, Park Ridge, Ill., assignor to Selected Glads, Inc., New Albany, Ind., a corporation of Tennessee Filed Sept. 30, 1966, Ser. No. 583,490
1 Claim. (Cl. Pl.—35)

My invention relates to a new and improved variety of gladiolus and is notable particularly for its small size, interesting blossom color contrast, distinctiveness and ability to perform well in all parts of the United States. I have identified this new variety as seedling #59–72 in my breeding work.

To the best of my knowledge, this variety is the result of a cross between an unnamed seedling, whose parents were Sprite and Carmen Corliss, and Topolino (all unpatented). Hand cross pollenization was done by me in my garden near Park Ridge, Ill., but no precaution was taken to prevent admixture by bees or insects.

This new variety has been asexually reproduced by me in Illinois and in California, by natural increase from cormels through several generations and its characteristics have proven to be permanently fixed.

The illustration, made a part of this application, shows a single bloom spike and plant, reduced in size, and is as nearly true to color as it is possible to depict. The illustration shows color, floret form and arrangement of florets on the flowerhead.

In the following detailed description, color plate references are to "The Horticultural Colour Chart" by the British Colour Council. Where there are other references to color, the ordinary dictionary meanings of the terms are intended.

*The plant*

Growth: Strong; grows to 48 inches in height over-all. Average propagator.

Blooming: Blooms in 85 days in the North from large bulbs.

Stems: Diameter of the stem is ⅜ inch. Color of the stem above the bulb is white.

Foliage: Bright green, upright and high-breaking. Leaves are 1½ inches across. Plant foliage, excluding the flower spike, is 36 inches high.

Disease resistance: Excellent resistance to known gladiolus diseases.

Corms: Round, plump, clean and healthy. Well-husked with thin, paper-like husk; straw colored. Flesh is Chinese Yellow $606_2$.

*The flower*

Spike: Flowerhead is 20 inches high with sixteen to seventeen buds of which five to six open at one time.

Bud:

*Size.*—Opening buds are 2½ inches long.

*Opening.*—Four buds show color at one time.

Flower:

*Arrangement.*—Florets are informally placed on the spike.

*Size.*—Individual florets are 2½ inches in diameter.

*Form.*—Round and ruffled.

*Keeping qualities.*—Good to excellent.

Petals:

*Shape.*—Ruffled and rounded.

*Size.*—Upper petal is 1½ inches across; lip petal, 1 inch.

*Aspect.*—Average substance.

*Fragrance.*—None.

*Color.*—Barium Yellow $503_2$. Reverse is deeper, $503_1$ to 503 at edges of fresh florets. Blotch is Dutch Vermilion $717_2$ to $717_1$ at darkest bisecting center line. Calyx is deep rose-red.

Reproduction organs:

*Stamens.*—Cream with bluish edges.

*Pistil.*—Cream.

*Comparisons*

My new variety resembles Sparkler (Plant Patent No. 1,741) more than any other variety, but differs from it principally as follows:

(1) New variety is a deeper yellow color.

(2) It has a larger blotch.

(3) It has a single red blotch, whereas Sparkler has a double red blotch on a deep buff throat.

(4) This variety is not needlepointed and recurved as is Sparkler.

(5) This variety is more prolific.

Having thus disclosed my new invention, I claim:

1. The new and distinct variety of gladiolus plant, substantially as herein shown and described, characterized by its small size, blossom color contrast and distinctiveness and ability to perform well in all parts of the United States.

No references cited.

ROBERT E. BAGWILL, *Primary Examiner.*